US00PP15311P2

(12) United States Plant Patent
Klemm

(10) Patent No.: US PP15,311 P2
(45) Date of Patent: Nov. 16, 2004

(54) ***GERANIUM* PLANT NAMED 'KLEP02038'**

(50) Latin Name: *Pelargonium peltatum*
Varietal Denomination: KLEP02038

(75) Inventor: Nils Klemm, Stuttgart (DE)

(73) Assignee: Klemm & Sohn GmbH & Co. K.G., Stuttgart (DE)

( * ) Notice: Subject to any disclaimer, the term of this patent is extended or adjusted under 35 U.S.C. 154(b) by 0 days.

(21) Appl. No.: 10/783,425

(22) Filed: Feb. 21, 2004

(51) Int. Cl.[7] ..... A01H 5/00
(52) U.S. Cl. ..... Plt./332
(58) Field of Search ..... Plt./332

*Primary Examiner*—Kent Bell
(74) *Attorney, Agent, or Firm*—C. A. Whealy

(57) ABSTRACT

A new and distinct cultivar of Ivy *Geranium* plant named 'KLEP02038', characterized by its trailing and roughly spherical plant habit; freely branching and vigorous plant habit; early flowering habit; red purple-colored double flowers arranged in umbels held above and beyond the foliage; and good tolerance to rain, wind and high temperatures.

1 Drawing Sheet

Botanical classification/cultivar designation: *Pelargonium peltatum* cultivar KLEP02038.

BACKGROUND OF THE INVENTION

The present invention relates to a new and distinct cultivar of Ivy *Geranium* plant, botanically known as *Pelargonium peltatum*, and hereinafter referred to by the name 'KLEP02038'.

The new Ivy *Geranium* is a product of a planned breeding program conducted by the Inventor in Stuttgart, Germany. The objective of the breeding program was to develop new Ivy *Geraniums* with uniform trailing and freely branching plant habit and interesting flower and foliage coloration.

The new Ivy *Geranium* originated from a cross-pollination made by the Inventor in 1998 of a proprietary selection of *Pelargonium peltatum* identified as code number GU 001, not patented, as the female, or seed, parent with 'Kleblue', disclosed in U.S. Plant patent application Ser. No. 09/250,014, now abandoned, as the male, or pollen, parent. The cultivar KLEP02038 was discovered and selected by the Inventor as a flowering plant within the resulting progeny from this cross-pollination in a controlled environment in Stuttgart, Germany, in 1999.

Asexual reproduction of the new cultivar by terminal cuttings taken in a controlled environment in Stuttgart, Germany since 2000 has shown that the unique features of this new Ivy *Geranium* are stable and reproduced true to type in successive generations of asexual reproduction.

SUMMARY OF THE INVENTION

The following traits have been repeatedly observed and are determined to be the unique characteristics of 'KLEP02038'. These characteristics in combination distinguish 'KLEP02038' as a new cultivar and distinguish it from other known Ivy *Geranium* cultivars:

1. Trailing plant habit.
2. Freely branching and vigorous plant habit.
3. Early flowering habit.
4. Red purple-colored double flowers.
5. Good tolerance to rain, wind and high temperatures.

Plants of the new Ivy *Geranium* are more vigorous and more freely branching than plants of the female parent, the selection GU 001. In addition, flowers of plants of the new Ivy *Geranium* are different in color than flowers of plants of the female parent. Plants of the new Ivy *Geranium* differ primarily from plants of the male parent, the cultivar Kleblue, in flower coloration.

Plants of the new Ivy *Geranium* can be compared to plants of the cultivar KLEP01042, disclosed in U.S. Plant Pat. No. 14,161. However, in side-by-side comparisons conducted in Stuttgart, Germany, plants of the new Ivy *Geranium* differed from plants of the cultivar KLEP01042 in the following characteristics:

1. Plants of the new Ivy *Geranium* were larger and more vigorous than plants of the cultivar KLEP01042.
2. Plants of the new Ivy *Geranium* and the cultivar KLEP01042 differed in flower color as plants of the cultivar KLEP01042 had dark red-colored flowers.

BRIEF DESCRIPTION OF THE PHOTOGRAPH

The accompanying colored photograph illustrates the overall appearance of the new cultivar, showing the colors as true as it is reasonably possible to obtain in colored reproductions of this type. Flower and foliage colors in the photograph may differ slightly from the color values cited in the detailed botanical description, which accurately describe the colors of the new Ivy *Geranium*. The photograph comprises a side perspective view of a typical flowering plant of 'KLEP02038' grown in a container.

DETAILED BOTANICAL DESCRIPTION

Plants of the cultivar KLEP02038 have not been observed under all possible environmental conditions. The phenotype may vary somewhat with variations in environment, such as temperature and light intensity, without, however, any variance in genotype.

The aforementioned photograph, following observations and measurements describe plants that were planted in containers in Stuttgart, Germany, and grown under commercial practice in a glass-covered greenhouse with day temperatures ranging from 18 to 22° C., night temperatures ranging from 14 to 17° C. and light levels ranging from 20,000 to 60,000 lux. Plants were pinched once during the production period. The photograph and botanical description were taken about 15 weeks after planting rooted young plants.

In the following description, color references are made to The Royal Horticultural Society Colour Chart, 1995 Edition, except where general terms of ordinary dictionary significance are used.

Botanical classification: *Pelargonium peltatum* cultivar KLEP02038.

Parentage:

*Female parent.*—Proprietary selection of *Pelargonium peltatum* identified as code number GU 001, not patented.

*Male parent.*—*Pelargonium peltatum* 'Kleblue,' disclosed in U.S. Plant patent application Ser. No. 09/250,014, abandoned.

Propagation:

*Type cutting.*—Terminal vegetative cuttings.

*Time to initiate roots.*—Summer: About 10 days at 22° C. Winter: About 11 days at 18 to 20° C.

*Time to produce a rooted young plant.*—Summer: About 17 days at 22° C. Winter: About 18 days at 18 to 20° C.

*Root description.*—Fine and white in color.

*Rooting habit.*—Freely branching.

Plant description:

*General appearance.*—Trailing plant habit; plants roughly spherical in shape; uniform; densely foliated.

*Growth and branching habit.*—Vigorous growth habit. Freely branching, about four to five lateral branches per plant.

*Plant height* (*to top of flower umbels*).—About 25 to 30 cm.

*Plant height* (*to top of foliar plane*).—About 20 to 25 cm.

*Plant width.*—About 18 to 24 cm.

*Lateral branches.*—Length: About 10 to 12 cm. Internode length: About 3 to 4 cm. Texture: Slightly pubescent. Color: 143B.

*Foliage description.*—Arrangement: Alternate, simple. Quantity of leaves per lateral branch: About six. Length: About 6 to 7 cm. Width: About 5 to 6 cm. Shape: Reniform with lobation. Apex: Rounded. Base: Peltate. Margin: Entire. Venation pattern: Palmate. Texture, upper and lower surfaces: Slightly pubescent. Color: Developing foliage, upper surface: 137B. Fully expanded foliage, upper surface: 147A. Developing foliage, lower surface: 137C. Fully expanded foliage, lower surface: 137B. Venation, upper and lower surfaces: 137C. Zonation pattern: Distance from margin to outer edge of zone: About 2 cm. Width: About 6 mm. Color 200A. Petiole: Length: About 2 to 3 cm. Diameter: About 2 mm. Color: 143B.

Flower description:

*Flower arrangement.*—Red purple-colored double flowers arranged in rounded hemispherical umbels arising from apical leaf axils. Umbels displayed above the foliage on upright peduncles. Flowers rounded in form. Umbels persistent, flowers not persistent. Flowers not fragrant.

*Quantity of flowers.*—Freely flowering habit; at full flower, plants have at least about four to five open and developing umbels with about six to ten flowers and flower buds per umbel.

*Flowering season.*—Year-round under greenhouse conditions. In the garden, flowering is continuous from spring until fall, with flowering heaviest during periods when night temperatures are 15 to 20° C.

*Time to flower.*—Early flowering; plants start flowering about 82 days after planting rooted young plants.

*Flower longevity.*—Flowers last about five to nine days on the plant.

*Umbel size.*—Height: About 8 to 10 cm. Diameter: about 8 to 10 cm.

*Flower size.*—Diameter: About 3 to 5 cm. Depth (height): About 2 cm.

*Flower buds.*—Length: About 8 to 12 mm. Diameter: About 4 to 5 mm. Shape: Elliptical. Color: 143B.

*Petals.*—Quantity per flower: About eight to ten. Length: About 2 cm. Width: About 10 to 12 mm. Shape: Obovate. Apex: Rounded. Base: Attenuate. Margin: Entire. Texture, upper and lower surfaces: Smooth, velvety. Color: When opening, upper surface: 59A. When opening, lower surface: 61B. Fully opened, upper surface: 60B, color becoming closer to 59A with development. Fully opened, lower surface: 61B; towards the base, 60B. Ventation, upper and lower surfaces: 61B.

*Petaloids.*—Quantity per flower: One to about five. Length: About 3 to 11 mm; irregular in size. Width: About 1 to 4 mm; irregular in size. Shape: Variable, irregular. Apex: Mostly rounded. Base: Attenuate. Margin: Mostly entire. Texture, upper and lower surfaces: Smooth, velvety. Color: Developing, upper surface: 59A. Developing, lower surface: 61B. Fully developed, upper surface: 60B; color becoming closer to 59A with development. Fully developed, lower surface: 61B. Venation, upper and lower surfaces: 59A.

*Sepals.*—Quantity per flower: Five, arranged in a single whorl. Length: About 5 to 8 mm. Width: About 3 to 6 mm. Shape: Elliptical. Apex: Acute. Margin: Entire. Texture, upper and lower surfaces: Rough. Color, upper surface: 143B. Color, lower surface: 143D.

*Peduncle* (*umbel stem*).—Length: About 18 to 20 cm. Diameter: About 4 mm. Angle: Erect. Strength: Moderately strong. Texture: Slightly pubescent. Color: 143B.

*Pedicel* (*individual flower stem*).—Length: About 2 to 3 cm. Diameter: About 1.5 mm. Angle: Erect. Strength: Strong. Texture: Smooth. Color: 143B overlain with 184D.

*Reproductive organs.*—Androecium: Anther quantity per flower: Five. Anther length: About 3 mm. Anther shape: Ovate. Anther color: 59B. Pollen amount: Moderate. Pollen color: 34B. Gynoecium: Pistil quantity per flower: One. Pistil length: About 5 mm. Stigma shape: Five-parted, star-shaped. Stigma color: 59B. Style length: About 5 mm. Style color: 73D. Ovary color: 138D.

*Seed/fruit.*—Seed and fruit production have not been observed.

Disease/pest resistance: Plants of the new Ivy *Geranium* have not been observed to be resistant to pathogens and pests common to Ivy *Geraniums*.

Weather tolerance: Plants of the new Ivy *Geranium* have been observed to tolerate rain, wind, and temperatures from about 7 to 32° C.

It is claimed:

1. A new and distinct cultivar of Ivy *Geranium* plant named 'KLEP02038', as herein illustrated and described.

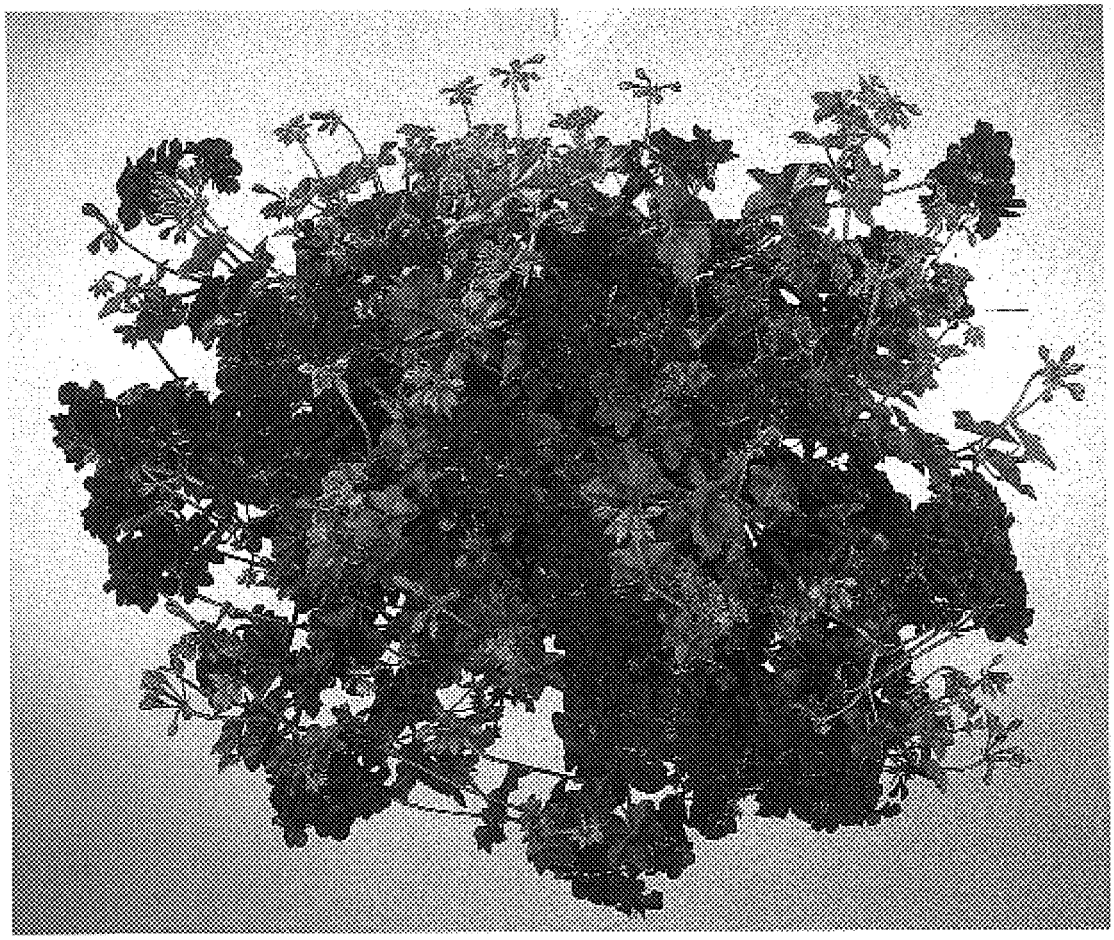

* * * * *